(12) United States Patent
Koh (10) Patent No.: US 9,393,545 B1
(45) Date of Patent: Jul. 19, 2016

(54) APPARATUS FOR TREATING FOOD WASTE

(71) Applicant: Chun Il Koh, Seoul (KR)

(72) Inventor: Chun Il Koh, Seoul (KR)

(*) Notice: Subject to any disclaimer, the term of this patent is extended or adjusted under 35 U.S.C. 154(b) by 0 days.

(21) Appl. No.: 14/676,818

(22) Filed: Apr. 2, 2015

(30) Foreign Application Priority Data

Feb. 17, 2015 (KR) .................. 10-2015-0023892

(51) Int. Cl.
*A61L 9/00* (2006.01)
*B01J 19/18* (2006.01)
*B01J 19/24* (2006.01)

(52) U.S. Cl.
CPC *B01J 19/18* (2013.01); *B01J 19/24* (2013.01); *B01J 2219/00049* (2013.01); *B01J 2219/24* (2013.01)

(58) Field of Classification Search
CPC .......... A61L 2/00; B02C 18/00; G05D 13/00; G05D 99/00; B09B 3/00
USPC ................ 422/105, 117, 243, 255, 307–309; 219/10.55 R
See application file for complete search history.

(56) References Cited

U.S. PATENT DOCUMENTS

| | | | | |
|---|---|---|---|---|
| 5,270,000 A | * | 12/1993 | Goldner | .................. A61L 11/00 180/309 |
| 7,735,761 B2 | | 6/2010 | Koh | |
| 7,762,713 B2 | | 7/2010 | Koh | |
| 2007/0196232 A1 | * | 8/2007 | Klaptchuk | .............. A61L 11/00 422/28 |

* cited by examiner

*Primary Examiner* — Monzer R Chorbaji
(74) *Attorney, Agent, or Firm* — Lee Patent International (57) ABSTRACT

The apparatus for treating food waste comprising an apparatus housing with a food waste input port formed on a top surface thereof; an open/close door that opens and closes the food waste input port; an open/close door operating device that operates the open/close door to be opened so as to open the food waste input port, or closed so as to close the food waste input port; and an automatic input device that enables at least part of an entrance of a food waste collection container to face with the food waste input port, in correspondence with the state of the open/close door.

16 Claims, 12 Drawing Sheets

| MENU | FUNCTION SETTING #2 | NEXT |

Shell Temp   45 deg          Auto Start Temp   10 deg
Water Temp   15 deg          Rev Time   4 sec

Weight Setting

Alert        300 lbs         M/C lbs    1300
Allowance    50  lbs         Food lbs   280
                             Set lbs    1420

| CLEAR | SET | RESET |

APPARATUS FOR TREATING FOOD WASTE

CROSS-REFERENCE TO RELATED APPLICATION

This application claims the benefit of Korean Patent Application No. 10-2015-0023892 filed on Feb. 17, 2015, the disclosures of which are incorporated herein by reference.

TECHNICAL FIELD

The embodiments described herein pertain generally to an apparatus for treating food waste.

BACKGROUND

Since organic waste like food waste generally contains a great deal of protein, carbohydrate, calcium and others, in addition to animal/vegetable fiber, if such organic waste is not decomposed to be dissipated and is buried, extracts from the organic waste are introduced into the underground, and thereby, contaminating underground water and others. Accordingly, for treating food waste, a food waste treating apparatus is generally used.

With respect to the food waste treating apparatus, Korean Patent Application No. 10-2008-0008421 describes an "apparatus for dissipation processing of food waste."

However, according to the described food waste treating apparatus, since a user needs to open and close an open/close door provided on a top side of a food waste input port by himself/herself, there has been inconvenience in that the user should directly put food waste into the food waste treating apparatus.

Especially, as the food waste treating apparatus has gradually become large in recent years due to the increasing capacity, the open/close door has been provided at a position beyond the scope of height that enables a user to open and close the open/close door by himself/herself, and thus, users have used tools such as a ladder in order to put food waste into the food waste treating apparatus.

In addition, according to the described food waste treating apparatus, when an excessive amount of food waste is injected into an apparatus housing, overload has occurred in a rotating shaft assembly being rotated within the apparatus housing, and thereby, causing damage thereto.

In addition, according to the described food waste treating apparatus, an amount of food waste to be put into the apparatus housing could not have been measured. Further, user's remote adjustment of the described food waste treating apparatus through a network has been restrictively accomplished.

SUMMARY

In view of the foregoing, the example embodiments provide an apparatus for treating food waste, which facilitates the input of food waste.

In an example embodiment, an apparatus for treating food waste is provided. The apparatus may include an apparatus housing with a food waste input port formed on a top surface thereof; an open/close door that opens and closes the food waste input port; an open/close door operating device that operates the open/close door to be opened so as to open the food waste input port, or closed so as to close the food waste input port; and an automatic input device that enables at least part of an entrance of a food waste collection container to face with the food waste input port, in correspondence with the state of the open/close door, wherein the automatic input device comprises a mounting plate, on which the food waste collection container is mounted, and which moves toward the food waste input port, a guide part, which guides the movement of the mounting plate, and an angle adjustment part, which adjusts an angle of the mounting plate.

In accordance with the example embodiments, it is possible to realize an apparatus for treating food waste, in which a food waste collection container is mounted on a mounting plate to automatically move toward a food waste input port, and the food waste collection container that has moved toward the food waste input port is automatically adjusted to an angle toward the food waste input port and rotated, such that the input of food waste is automatically accomplished. As a result, utility and usability of the apparatus for treating food waste can increase.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

In the detailed description that follows, embodiments are described as illustrations only since various changes and modifications will become apparent to those skilled in the art from the following detailed description. The use of the same reference numbers in different figures indicates similar or identical menus.

DETAILED DESCRIPTION

Hereinafter, example embodiments will be described in detail with reference to the accompanying drawings so that inventive concept may be readily implemented by those skilled in the art. However, it is to be noted that the present disclosure is not limited to the example embodiments but can be realized in various other ways. In the drawings, certain parts not directly relevant to the description are omitted to enhance the clarity of the drawings, and like reference numerals denote like parts throughout the whole document.

Throughout the whole document, the terms "connected to" or "coupled to" are used to designate a connection or coupling of one element to another element and include both a case where an element is "directly connected or coupled to" another element and a case where an element is "electronically connected or coupled to" another element via still another element.

Throughout the whole document, the term "on" that is used to designate a position of one element with respect to another element includes both a case that the one element is adjacent to the another element and a case that any other element exists between these two elements.

Throughout the whole document, the term "comprises or includes" and/or "comprising or including" used in the document means that one or more other components, steps, operations, and/or the existence or addition of elements are not excluded in addition to the described components, steps, operations and/or elements. Throughout the whole document, the terms "about or approximately" or "substantially" are intended to have meanings close to numerical values or ranges specified with an allowable error and intended to prevent accurate or absolute numerical values disclosed for understanding of the present invention from being illegally or unfairly used by any unconscionable third party. Through the whole document, the term "step of" does not mean "step for."

For reference, in the descriptions of example embodiments, terms related to directions or positions (an upper portion, a lower portion, etc.) have been defined based on the position state of each component shown in the drawings. For example, in FIG. 1A, the 12 o'clock direction may be generally the upper portion, and the 6 o'clock direction may be generally the lower portion.

Examples embodiments relate to an apparatus for treating food waste.

First, an apparatus for treating food waste in accordance with an example embodiment (hereinafter, referred-to as the "present food waste treating apparatus") is described.

Figure 1A:
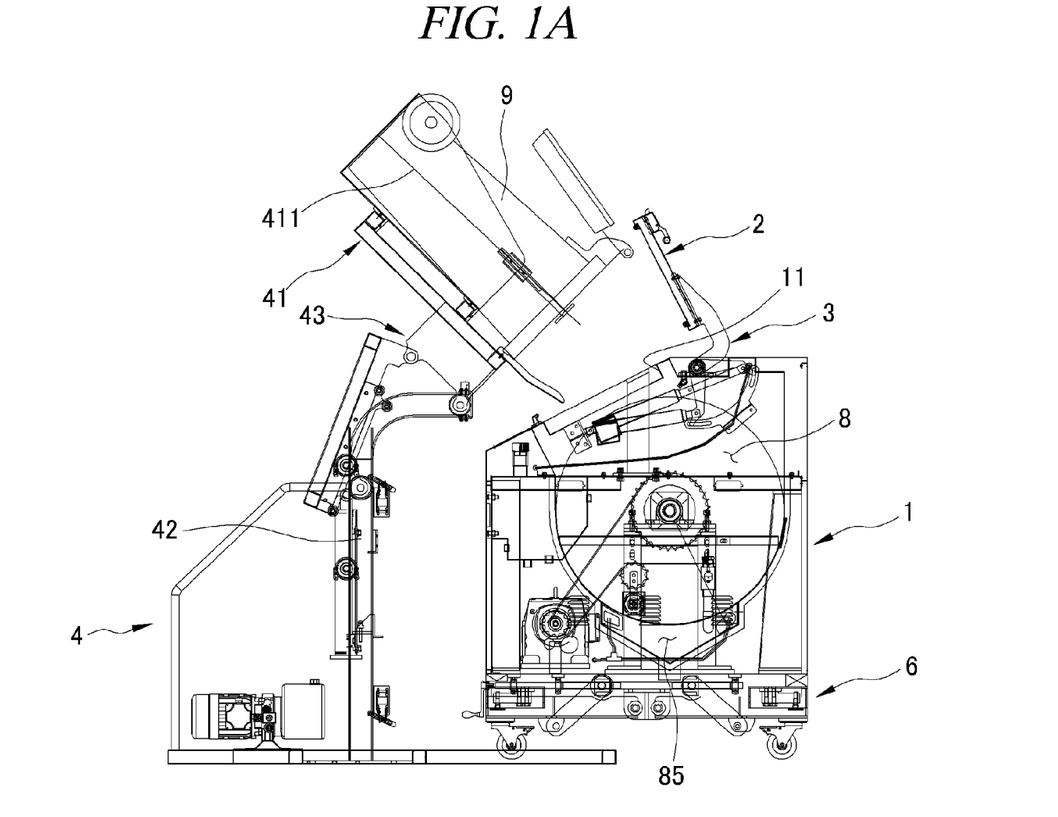
FIG. 1A is a schematic conceptual view showing the state that food waste within a food waste collection container is being sent to an apparatus housing, in an apparatus for treating food waste in accordance with an example embodiment.

With reference to FIG. 1A, the present food waste treating apparatus includes an apparatus housing 1 with a food waste input port 11 formed on a top surface thereof, an open/close door that opens and closes the food waste input port 11, and an open/close door operating device 3 that operates the open/close door 2 to be opened so as to open the food waste input port 11, or closed so as to close the food waste input port 11.

Since the open/close door 2 can be operated to be opened or closed by the open/close door operating device 3, it is possible to avoid the inconvenience caused because a user has to directly open or close the open/close door 2.

In addition, the present food waste treating apparatus includes an automatic input device 4, which enables at least part of an entrance of the food waste collection container to face with the food waste input port 11, in correspondence with the state of the open/close door 2.

Enabling at least part of the entrance of the food waste collection container 9 to face with the food waste input port 11 may mean enabling at least part of the entrance of the food waste collection container to be directed toward the food waste input port 11, so as to enable food waste in the food waste collection container 9 to be sent into the food waste input port 11.

In accordance with the present food waste treating apparatus, since the automatic input device 4 inputs food waste into the apparatus housing 1 in correspondence to the state of the open/close door 2, a user does not need to directly input food waste into the apparatus housing 1.

Conventionally, a user has directly opened and closed the open/close door 2 of the food waste treating apparatus, and directly input food waste into the food waste treating apparatus. However, as the food waste treating apparatus has become large, the open/close door 2 has been positioned beyond the scope of height that enables the user to directly open and close the open/close door 2, so that it has become difficult for a user to directly open and close the open/close door 2, or input food waste into the food waste treating apparatus.

Through the present food waste treating apparatus, the open/close door 2 is automatically operated to be opened and closed and food waste can be automatically sent to the apparatus housing 1 by the automatic input device 4. So, user's convenience and safety is improved.

Hereinafter, the automatic input device 4 is described in detail.

Figure 1B:
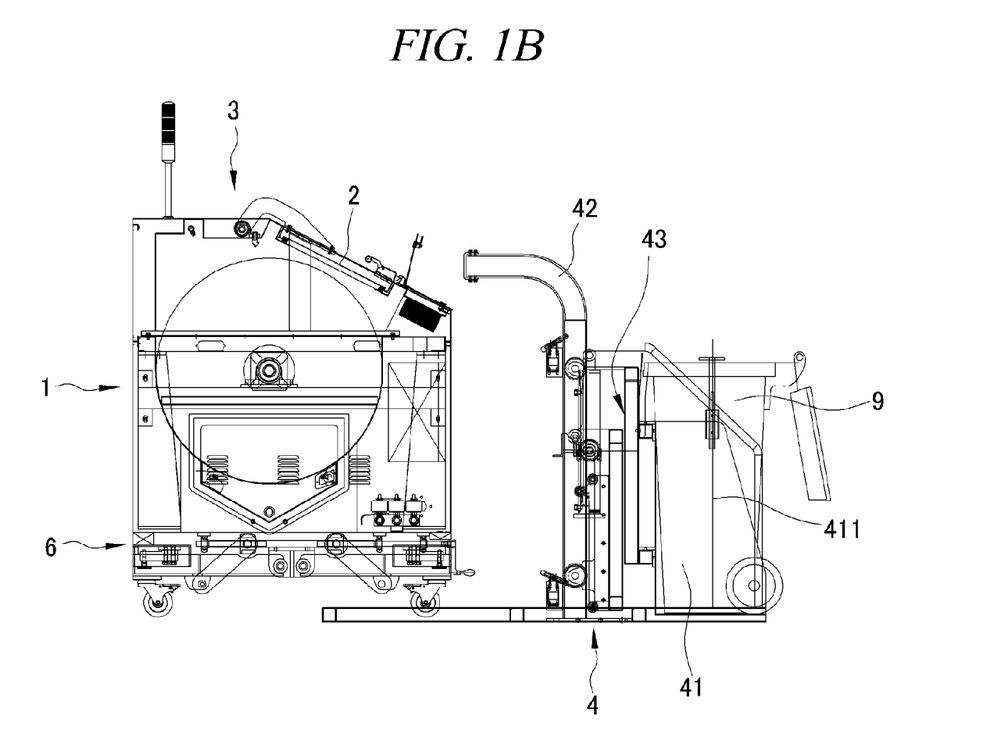
FIG. 1B is a schematic conceptual view showing the state immediately after the food waste collection container is mounted on a mounting plate, in an apparatus for treating food waste in accordance with an example embodiment.

With reference to FIG. 1A and FIG. 1B, the automatic input device 4 includes a mounting plate 41, on which the food waste collection container 9 containing food waste is mounted, and which moves from an initial position toward the food waste input port 11.

As shown in FIG. 1A and FIG. 1B, the mounting plate 41 may include a holding member 411, to hold the food waste collection container 9 to be mounted on the mounting plate 41.

In addition, as shown in FIG. 1B, the initial position of the mounting plate 41 may mean a position of the mounting plate 41 when the food waste collection container 9 is mounted on the mounting plate 41.

In addition, as described above, the automatic input device 4 inputs food waste into the food waste input port 11 in correspondence with the state of the open/close door 2. This is specifically described below.

In the automatic input device 4, which inputs food waste into the food waste input port 11 in correspondence to the state of the open/close door 2, once the opening operation of the open/close door 2 is completed, the mounting plate 41 may move from the initial position toward the food waste input port 11.

In addition, when the mounting plate 41 moves from the food waste input port 11 toward the initial position, the open/close door operating device 3 may operate the open/close door 2 to be closed.

For example, the open/close door 2 may be operated to be closed, from the time that the mounting plate 41 spacing from the food waste input port 11 begins to be located at the position that does not interfere the closing operation of the open/close door 2.

As described, the input of food waste and the opening and closing of the food waste input port 11 may be cooperatively operated.

In addition, with reference to FIG. 1A and FIG. 1B, the automatic input device 4 may include a guide rail part 42, which guides the movement of the mounting plate 41. The guide rail part 42 may be formed from a lower end portion of the apparatus housing 1 to the food waste input port 11.

With reference to FIG. 1A and FIG. 1B together, the mounting plate 41 may move along the guide rail part 42.

In addition, the automatic input device 4 includes an angle adjustment part 43, which adjusts an angle of the mounting plate 41. The angle of the mounting plate 41 may mean an angle formed between the mounting plate 41 and the food waste input port 11.

The angle adjustment part 43 may adjust the angle of the mounting plate 41 to enable the food waste collection container 9 mounted on the mounting plate 41 to be directed toward the food waste input port 11.

In addition, if necessary, the angle adjustment part 43 may rotate the mounting plate 41 a multiple number of times within a preset angle range, such that food waste in the food waste collection container 9 mounted on the mounting plate 41 does not remain in the food waste collection container 9.

Here, the preset angle range may mean a range, which enables shaking of food waste in the food waste collection container 9, when the food waste collection container 9 is rotated. For example, the angle adjustment part 43 may rotate the mounting plate 41 within a range of from an angle or larger formed between the food waste collection container 9 and the food waste input port 11 when the food waste collection container 9 mounted on the mounting plate 41 is positioned in parallel with the ground, to an angle or smaller formed between the food waste collection container 9 and the food waste input port 11 when the food waste collection container 9 is positioned vertically to the ground.

For example, when the angle adjustment part 43 is rotated once such that the mounting plate 41 is directed toward the food waste input port 11, part of food waste in the food waste collection container 9, especially, food waste remaining in a bottom surface of the food waste collection container 9 may not be sent to the apparatus housing 1.

However, in accordance with the present food waste treating apparatus, the angle adjustment part 43 rotates the mounting plate 41 a plurality of times within the preset angle range, so that entire food waste in the food waste collection container 9 can be sent to the apparatus housing 1.

Figure 2:
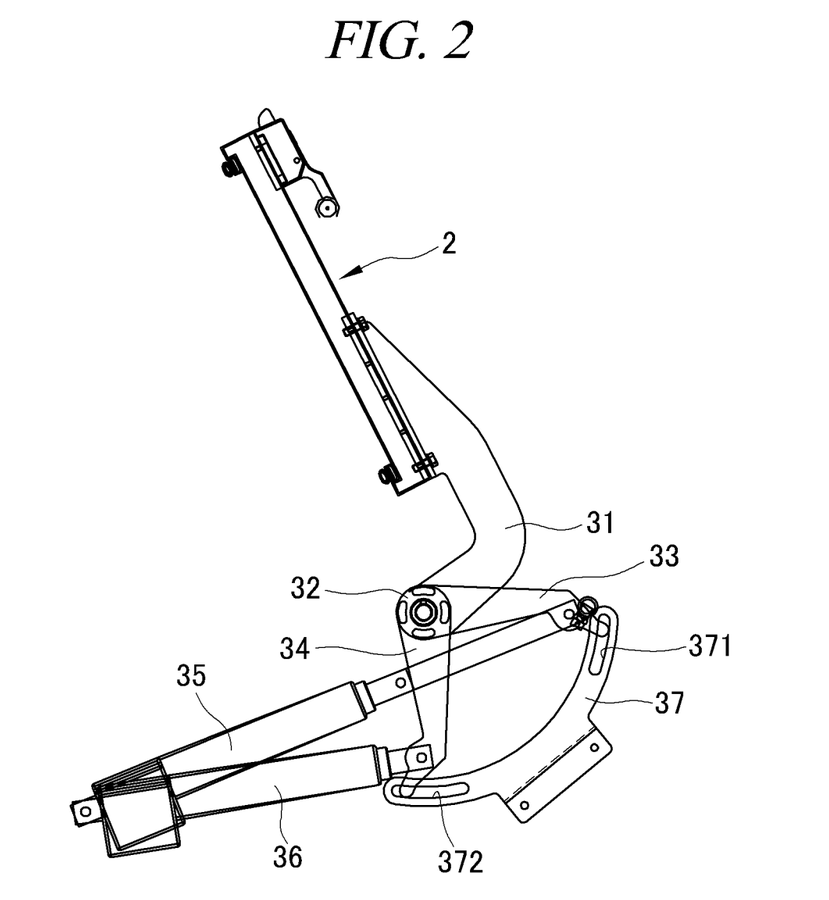
FIG. 2 is a schematic conceptual view showing an open/close door operating device immediately after an open/close door is operated to be opened.

In addition, with reference to FIG. 2, the open/close door operating device 3 may include an inner operation lever 31, which extends from a rear surface of the open/close door to a downward direction, a rotating shaft 32, which is provided at an end of the inner operation lever 31, a first outer operation lever 33, which extends from the rotating shaft 32, and of which an end moves, a second outer operation lever 34, which extends from the rotating shaft 32, and of which an end moves, a first power part 35, which is connected to the end of the first outer operation lever 33 to move the end of the first outer operation lever 33, a second power part 36, which is connected to the end of the second outer operation lever 34 to move the end of the second outer operation lever 34, and a guide part 37 provided with a first rail 371 and a second rail 372 for guiding the movement of the end of the first outer operation lever 33 and the end of the second outer operation lever 34. In this case, the rotating shaft 32 may be rotated by the first outer operation lever and the second outer operation lever 34.

Specifically, as shown in FIG. 2, once the first outer operation lever 33 moves in the uppermost direction of the first rail 371 by the first power part 35, and the second outer operation lever 24 moves in the lowermost direction of the second rail 372 by the second power part 36, the rotating shaft 32 may be rotated such that the open/close door 2 is operated to be opened.

In case of the closing operation of the open/close door 2, with reference to FIG. 2, once the first outer operation lever 33 moves in the lowermost direction of the first rail 371 by the first power part 35, and the second outer operation lever 34 moves in the uppermost direction of the second rail 372 by the second power part 36, the rotating shaft 32 may be rotated such that the open/close door 2 is operated to be closed.

Hereinafter, the apparatus housing 1 is described in detail.

With reference to FIG. 1A to FIG. 3, the apparatus housing 1 may include the mixing basin 8, into which the food waste sent through the food waste input port 11. In addition, with reference to FIG. 1A and FIG. 1B, the apparatus housing 1 may include a washing room 85 provided at a lower side of the mixing basin 8.

Figure 3:
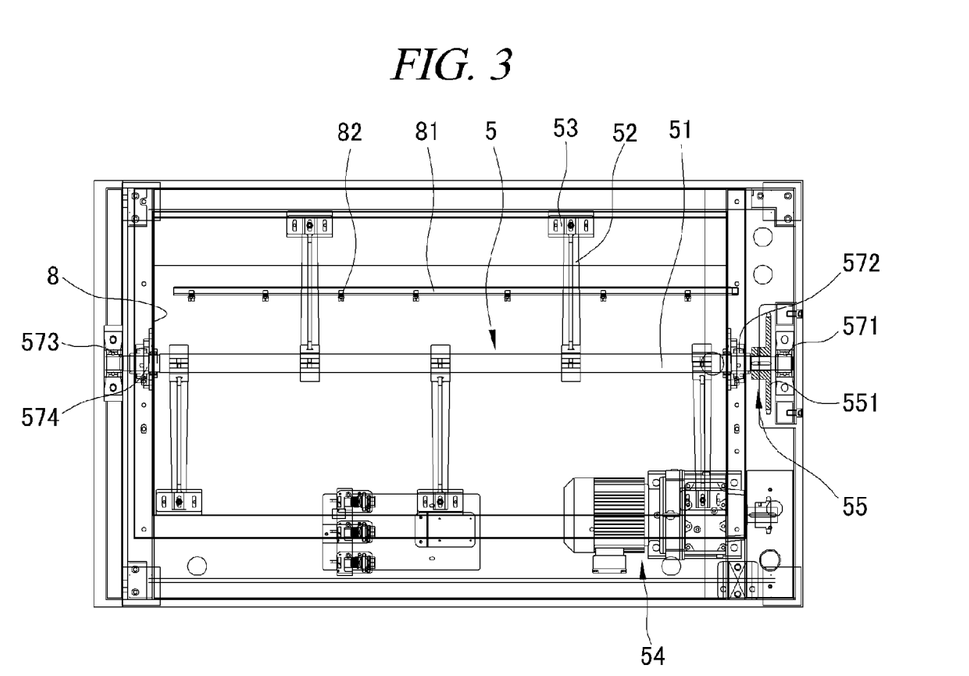
FIG. 3 is a schematic conceptual view when the inside of a mixing basin is viewed from an upper portion, in an apparatus for treating food waste in accordance with an example embodiment.

With reference to FIG. 3, the present food waste treating apparatus may include a rotating shaft assembly 5, which is provided in the inside of the apparatus housing 1 to stir food waste within the apparatus housing 1. Specifically, as shown in FIG. 3, the rotating shaft assembly 5 may be provided within the mixing basin 8.

Specifically, as shown in FIG. 3, the rotating shaft assembly 5 may include a rotating shaft 51, a plurality of agitating paddle support bars 52, which are spaced from one another and extend from the rotating shaft 51 in a vertical direction to the rotating shaft 51, an agitating paddle 53, which is provided at an end of each of the agitating paddle support bars 52, a motor 54, which provides power for rotating the rotating shaft 51, and a power transmission structure 55, which transmits the power of the motor 54 to the rotating shaft 51.

As food waste is stirred by rotation of the agitating paddle support bars 52 and the agitating paddles 53, it is possible to avoid the phenomenon that food waste is pushed to one side within the apparatus housing 1.

The agitating paddle 53 may be provided at the agitating paddle support bar 52 by an engagement member 56.

The engagement member 56 may be a bolt. In addition, the engagement member 56 may be embodied in a casting mold.

Figure 4:
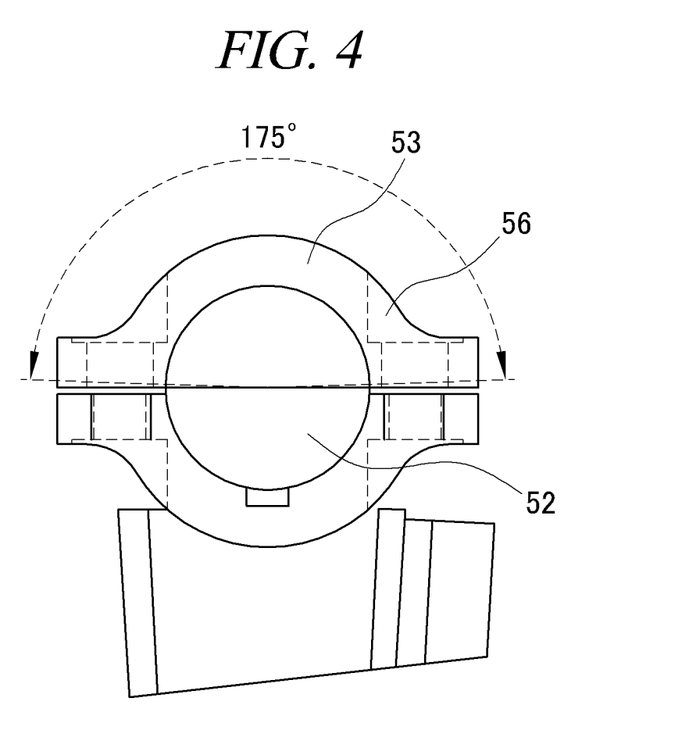
FIG. 4 is a schematic conceptual view showing an angle formed by a contact surface between an agitating paddle and an agitating paddle support bar, in an apparatus for treating food waste in accordance with an example embodiment.

Accordingly, with reference to FIG. 4, a contact area between the agitating paddle 53 and the agitating paddle support bar 52 may increase.

Conventionally, the engagement member (engagement bolt) connecting the agitating paddle and the agitating paddle support bar has been manufactured in a press bending manner. Accordingly, an angle formed by a contact area between the agitating paddle 53 and the agitating paddle support bar 52 has been 130°. As such, there has been a problem in that the engagement member engaging the agitating paddle 53 and the agitating paddle support bar 52 is loosened.

However, in accordance with the present food waste treating apparatus, since the engagement member engaging the agitating paddle 53 and the agitating paddle support bar 52 is embodied as a casting mold, the contact area increases, so that the angle formed by the contact area can increase to 175°, as shown in FIG. 4. Accordingly, tight engagement between the agitating paddle 53 and the agitating paddle support bar 52 can be accomplished.

In addition, the engagement member 56 may be applied to engagement between the agitating paddle support bar 52 and the rotating shaft 51.

In addition, when load higher than a normal value occurs in the motor 54, the rotating shaft 51 may be reversely rotated at a preset angle.

For example, if an excessive amount of food waste is put into the apparatus housing 1, so that the agitating paddle support bars 52 and the agitating paddles 53 are caught in the food waste, load higher than a normal value may occur in the motor 54, which provides power to the rotating shaft 51 in order to rotate the agitating paddle support bars 52 and the agitating paddles 53, and other components as well as the motor 54 may also be damaged. This damage results in significant loss of time and money.

As described, when load higher than a normal value occurs in the motor 54 that is providing power to the rotating shaft 51, an inverter (not illustrated in the drawings) of the motor 54 senses the load higher than a normal value and the rotating shaft 51 may be reversely rotated at a preset angle. Accordingly, the agitating paddle support bars 52 and the agitating paddles 53 are reversely rotated so that they can escape from the jam by the food waste, and occurrence of damage to the motor 54 can be prevented.

For example, the rotating shaft 51 may be reversely rotated at an angle of 90°. However, the preset angle is not limited thereto, and may be set within a range of from 0° or more to less than 360° according to the rotational conditions.

In addition, when load higher than a normal value occurs in the motor 54, the rotation of the rotating shaft 51 may be stopped.

Accordingly, a user may eliminate a cause for the occurrence of the load higher than a normal value in the motor 54.

In addition, once a cause for the occurrence of the load higher than a normal value in the motor 54 is eliminated, the rotating shaft 51 may run again. The rerunning of the rotating shaft 51 may be automatically implemented, or manually implemented by a user.

In addition, when a problem occurs in the rotation of the agitating paddle support bars 52 and the agitating paddles 53, for example, when load higher than a normal value occurs in the motor 54 rotating the rotating shaft 51, an alarm message may appear on the touch screen 7, which will be described later. Through the alarm message, a user may figure out the state of the agitating paddle support bars 52 and the agitating paddles 53 to resolve the problem.

Figure 5:
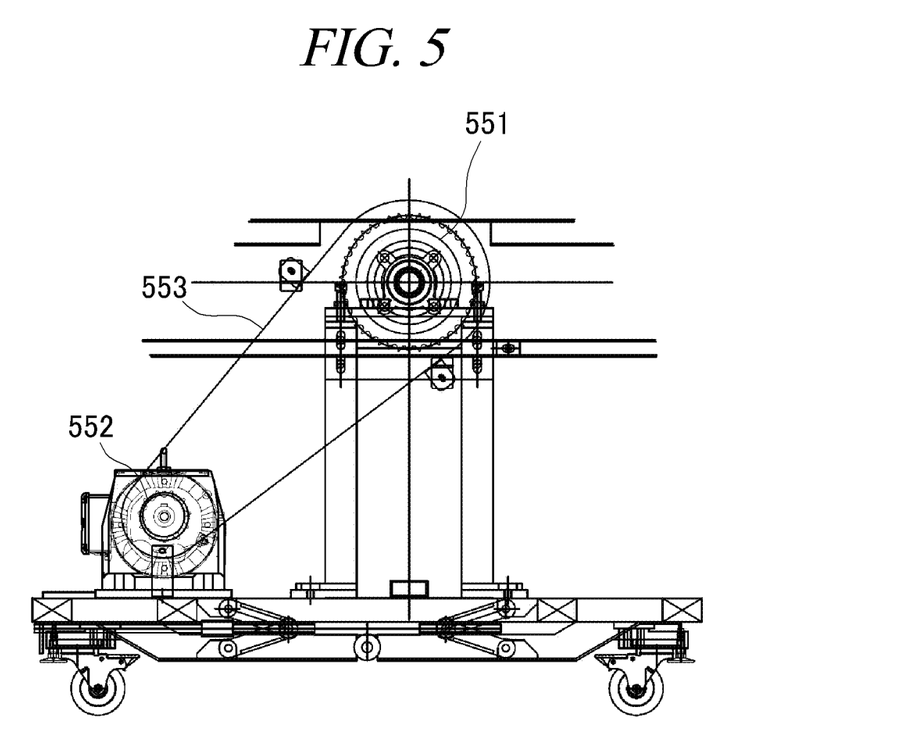
FIG. 5 is a schematic conceptual view when a power transmission structure is viewed from one side in order to describe the power transmission structure, in an apparatus for treating food waste in accordance with an example embodiment.

In addition, with reference to FIG. 3 and FIG. 5 together, the power transmission structure 55 may include an interlocking sprocket 551, which is provided along an outer circumstance of one end (refer to FIG. 3; an end part directed toward the 3 o'clock direction) of the rotating shaft 51, a driving sprocket 552, which is provided at the rotating shaft of the motor 54, and a closed-figure-shaped chain 553, which is provided across part of the outer circumference of the interlocking sprocket 551 and part of the outer circumference of the driving sprocket 552, so as to enable the interlocking sprocket 551 and the driving sprocket 552 to cooperatively work with each other.

Accordingly, when the motor 54 operates such that the driving sprocket 552 is rotated, the interlocking sprocket 551 may be rotated. Once the interlocking sprocket 551 is rotated, the rotating shaft assembly 5 is rotated such that the agitating paddles 53 may be rotated together with the agitating paddle support bars 52.

In addition, the rotating shaft assembly 5 may include a plurality of bearings 571, 572, which are provided along a circumference of an outer circumference surface of one end of the rotating shaft 51, and a plurality of bearings 573, 574, which are provided along a circumference of an outer circumference surface of the other end (refer to FIG. 3; the end part directed toward the 9 o'clock direction) of the rotating shaft 51.

Accordingly, damage to the rotating shaft 51 and the power transmission structure 55 can be prevented.

In addition, a plurality of the bearings 57 arranged in one end of the rotating shaft 51 may be arranged sandwiching the interlocking sprocket 551.

For example, as shown in FIG. 3, bearings 571, 572, 573 and 574 may be provided in pairs at one end and the other end of the rotating shaft 51, respectively. The two (2) bearings 571 and 572 may be arranged at one end of the rotating shaft 51 and positioned to each side of the coupled sprockets 551.

In addition, although not explicitly illustrated in the drawings, the power transmission structure 55 may include a roller-type tension device. The roller-type tension device may control tension of the chain 553.

For example, once the motor 54 operates such that the driving sprocket 552 is rotated, the chain 553 is revolved by the roller-type tension device, and the tension of the chain 553 may be controlled.

Figure 6:
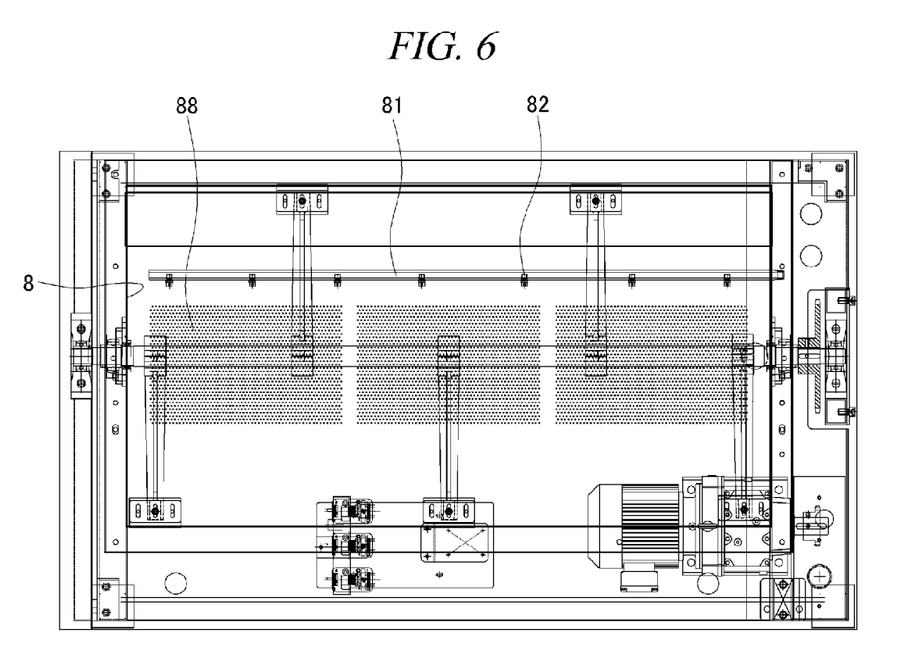
FIG. 6 is a schematic conceptual view when the inside of the mixing basin is viewed from an upper portion in order to describe a discharge hole, in an apparatus for treating food waste in accordance with an example embodiment.

In addition, as described above, food waste stirred and decomposed by the agitating paddles 53 are injected in advance into the mixing basin 8 to be decomposed by existing microorganisms and (biodegradable and non-degradable) materials, and leachate generated at the time of the decomposition may be discharged through a drain hole 88.

With reference to FIG. 1A and FIG. 1B, the food waste discharged through the drain hole 88 drops down to be collected into the washing room 85, and leachate collected into the washing room 85 may be discharged to an outside BOD purifying device (not explicitly illustrated) through a drain pipe.

As described, once the stirring and the drying of the food waste are completed, the completely stirred and decomposed food waste residuals may be discharged to the outside of the apparatus housing 1 through a discharge port or a discharging device, though it is not explicitly illustrated, so that they may be utilized as compost for plant cultivation and others.

In addition, the present food waste treating apparatus may include a hot water spraying and supplying device 81.

Once the food waste is removed from the mixing basin 8, the hot water spraying and supplying device 81 sprays hot water that has been filled and heated in a hot water tank through a hot water spray nozzle 82 at a high pressure, so as to thoroughly remove the food waste residuals within the mixing basin 8.

The hot water introduced into the mixing basin 8 through the hot water spray nozzle 82 may be introduced into the washing room 85 through the drain hole 88 together with the food waste to be removed. In addition, the foreign materials and the hot water introduced into the washing room 85 are discharged to an outside BOD purifying device or the like.

As described, after the bottom surface of the mixing basin 8 is cleaned, the washing room 85 may be subject to cleaning and sterilization processing by a washing room cleaning device and a sterilization processing device.

For reference, the hot water spraying and supplying device 81 and the washing room cleaning device may work, when food waste is stirred.

Meanwhile, with reference to FIG. 1A and FIG. 1B, the present food waste treating apparatus may include a load cell 6, which is provided at the lower end portion of the apparatus housing 1, to measure weight of food waste injected into the apparatus housing 1.

Here, the weight of the food waste injected into the apparatus housing 1 may mean at least one of an amount of food waste put into the apparatus housing 1 and an amount of food waste stored within the apparatus housing 1. In addition, the weight of the food waste measured by the load cell 6 may be displayed on the touch screen 7, which is described below.

Hereinafter, the touch screen 7 is described in detail.

Figure 7:
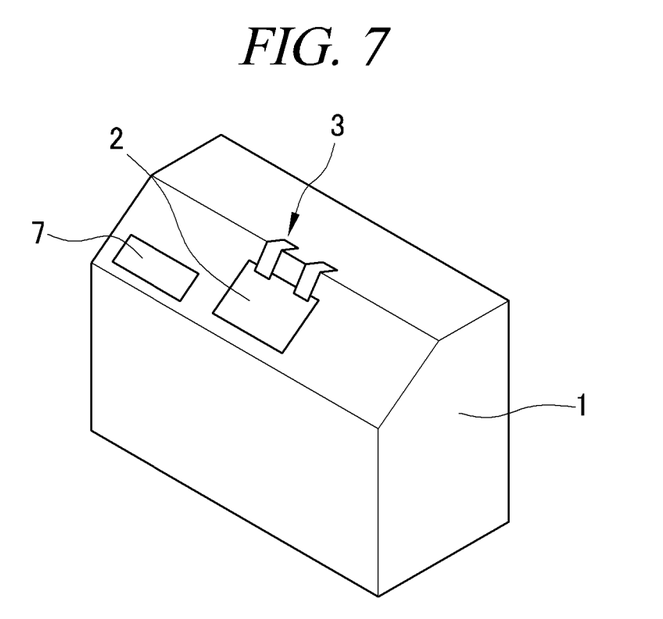
FIG. 7 is a schematic perspective view of an apparatus for treating food waste in accordance with an example embodiment.

With reference to FIG. 7, the present food waste treating apparatus may include the touch screen 7, which is provided on an external surface of the apparatus housing 1 to display a plurality of operation menus, and enable selection of the operation menus to be displayed.

The touch screen 7 may display operation menus, and a user may select the menus through the touch screen.

Figure 8:
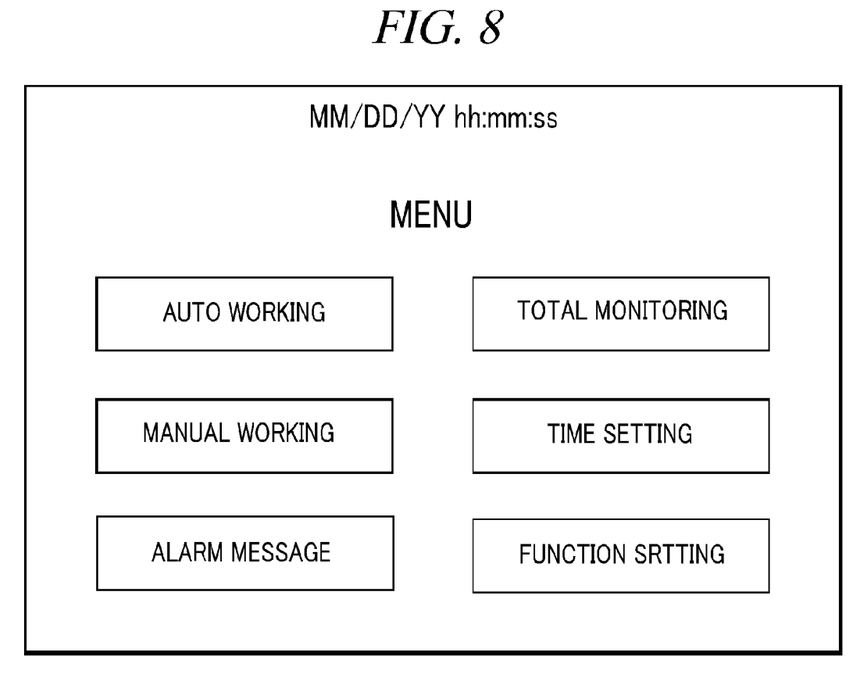
FIG. 8 is a schematic conceptual view of a main screen of a touch screen.

Specifically, with reference to FIG. 8, a main screen of the touch screen 7 may display a menu for automatic working of the present food waste treating apparatus (Auto Working), a menu for displaying the general working state of the present food waste treating apparatus (Total Monitoring), a menu for test operation of each function of the present food waste treating apparatus (Manual Working), a menu for setting a parameter for working of the present food waste treating apparatus (Time Setting), a menu for displaying an alarm message (Alarm Message), and a menu for setting each function (Function Setting).

Figure 9:
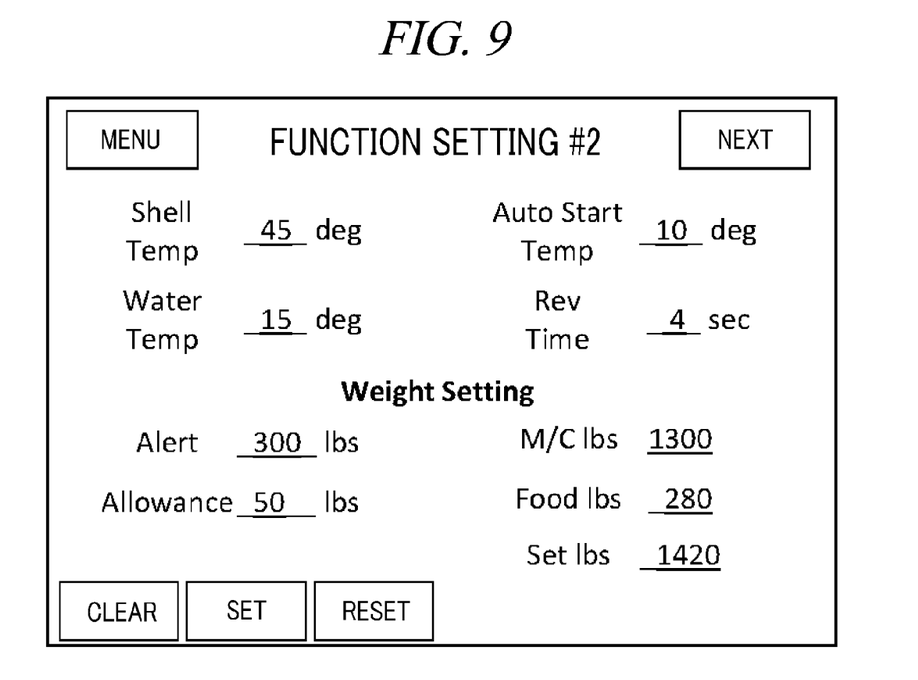
FIG. 9 is a schematic conceptual view of a screen displayed on the touch screen, when a menu for setting each function on the main screen of the touch screen is selected.

When the menu for setting each function is selected, a menu for a temperature within the mixing basin (Shell Temp) may be displayed, as shown in FIG. 9.

With reference to FIG. 9, in the menu for a temperature within the mixing basin, the temperature in the inside of the mixing basin 8 may be set. If the temperature within the mixing basin 8 is higher than a set temperature, a microbial agent within the mixing basin 8 may not work, and thus, the working of the present food waste treating apparatus may be stopped for a while.

In addition, as shown in FIG. 9, when the menu for setting each function is selected, an automatic start temperature menu (Auto Start Temp) may be displayed.

With reference to FIG. 9, in the automatic start temperature menu, the lowest temperature, at which the present food waste treating apparatus works, may be set. That is, the present food waste treating apparatus may work when the temperature range of the mixing basin 8 falls between a temperature set in the automatic start temperature menu and a temperature set in the menu for a temperature within the mixing basin.

In addition, when the menu for setting each function is selected, a menu for setting reverse rotation time (Rev Time) may be displayed, as shown in FIG. 9.

With reference to FIG. 9, in the menu for setting reverse rotation time, when the agitating paddle support bars 52 and the agitating paddles 53 are caught in food waste, and thus, overload occurs in the motor 54, time for reverse rotation may be set. For example, if the time for reverse rotation is set to four (4) seconds, the rotating shaft 51 may be rotated by ¼ (90°) in a reverse direction.

In addition, when the menu for setting each function is selected, a menu for weight setting may be displayed, as shown in FIG. 9. Through the menu for weight setting, the working of the load cell 6 may be set.

More specifically, with reference to FIG. 9, in the menu for weight setting, an alert menu (Alert) and an allowance menu (Allowance) may be displayed. In the alert menu, an amount of food waste that can be injected into the housing apparatus 1 at one time may be set.

For example, if the present food waste treating apparatus should treat 1,500 pounds of food waste for a day and food waste is put into the present food waste treating apparatus five (5) times a day, 300 pounds of food waste should be put into the present food waste treating apparatus at one time. In this case, the alert menu is set to 300, as shown in FIG. 9.

In addition, the allowance menu is a supplementary (buffer) menu for eliminating an error of measuring heavier weight than actual weight in the load cell 6, due to impact caused when the open/close door 2 is operated to be opened and closed. That is, with reference to FIG. 9, if the allowance menu describes 50, it means that 50 pounds may be added to the alert menu.

A value obtained from summing the weights set in the alert menu and the allowance menu may mean a maximum amount of food waste that can be introduced into the apparatus housing 1 at one time.

If more food waste than the value set in the alert menu and the allowance menu is put into the food waste treating apparatus, the automatic working of the present food waste treating apparatus may be stopped. In this way, putting an excessive amount of food waste by the user can be prevented.

In addition of the menus displayed in the menu for weight setting, menus other than the alert menu and the allowance menu may allow setting basic values required to measure weight of food waste.

That is, the touch screen 7 may display menus for setting weight values to set a maximum amount of each input and a compensational value for the input of food waste, compared to weight of food waste measured by the load cell 6.

In addition, a user may modify and set at least one of the above-described menus through the touch screen 7.

At least one of the above-described menus may be set to lock. This lock setting is intended to enable only a manager of the present food waste treating apparatus to set and modify the menu set to lock.

Figure 10:
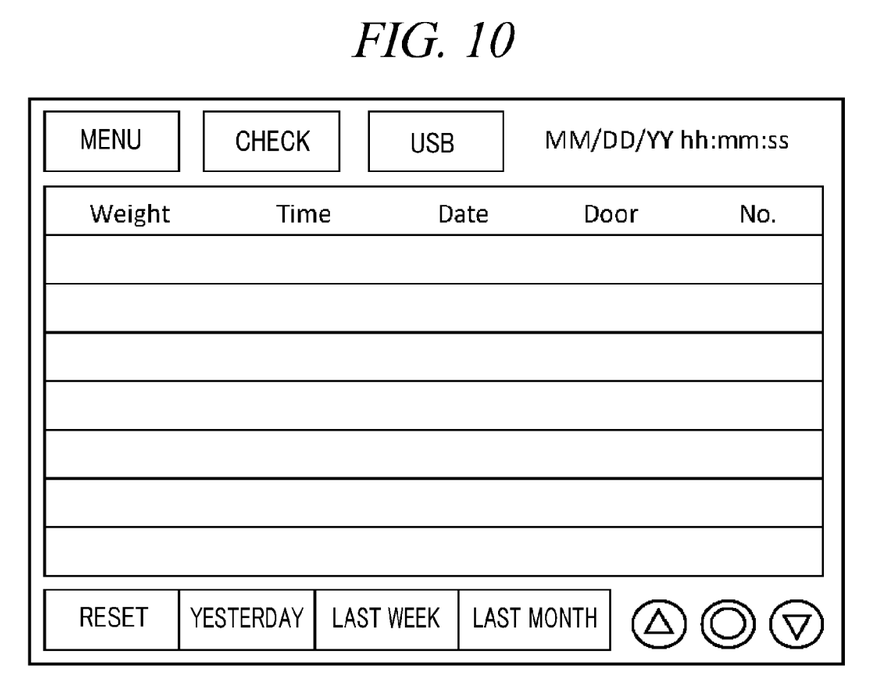
FIG. 10 is a schematic conceptual view of the screen of the touch screen that displays a log menu, which records an amount of food waste measured by a load cell.

In addition, with reference to FIG. 10, the touch screen 7 may display a log menu, which records an amount of food waste measured by the load cell 6. This log menu may be accessed through the menu for displaying the general working state of the present food waste treating apparatus (Total Monitoring). Through the log menu, an amount of food waste that a user has treated by using the present food waste treating apparatus may be displayed by days, weeks, and months. In addition, through the log menu, costs saved in treating food waste may also be displayed.

Figure 11:
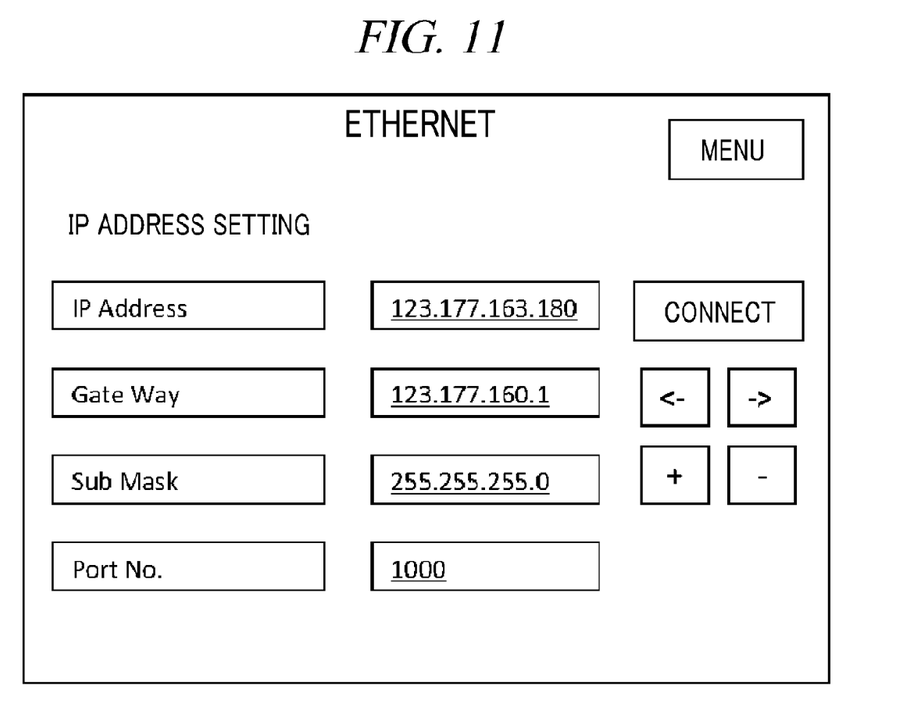
FIG. 11 is a schematic conceptual view of a screen displayed on the touch screen 7, when a power line communication (PLC) Ethernet card is mounted in an apparatus for treating food waste in accordance with an example embodiment.

Meanwhile, with reference to FIG. 11, the present food waste treating apparatus may include a power line communication (PLC) Ethernet card.

Accordingly, state information of the present food waste treating apparatus may be collected by an external server through internet network service.

Specifically, the state information of the present food waste treating apparatus may correspond to general state information of the present food waste treating apparatus, such as an amount of food waste injected, an amount of food waste treated, an amount of water used, and an amount of electricity consumed.

In addition, the state of the present food waste treating apparatus may be remotely monitored and remotely controlled through a network.

Especially, in countries such as the USA, the present food waste treating apparatus may be leased, and in this case, an amount of food waste treated by the present food waste treating apparatus may be transmitted to or stored in an external server through the network service, and an invoice may be issued and charged to a user according to the transmitted or stored information.

In addition, since an amount of food waste treated by the present food waste treating apparatus may be measured on a daily, weekly or monthly basis as described above, costs may be charged to a user on a daily, weekly or monthly basis.

Once the power line communication (PLC) Ethernet card is mounted in the present food waste treating apparatus, the touch screen 7 may display the screen illustrated in FIG. 11, and the state information of the present food waste treating apparatus may be transmitted to or stored in an external server through internet network service, through setting on the illustrated screen.

That is, the touch screen 7 may display a screen to enable the state information of the present food waste treating apparatus to be transmitted to or stored in an external server through an internet network service.

The above description of the example embodiments is provided for the purpose of illustration, and it would be understood by those skilled in the art that various changes and modifications may be made without changing technical conception and essential features of the example embodiments. Thus, it is clear that the above-described example embodiments are illustrative in all aspects and do not limit the present disclosure. For example, each component described to be of a single type can be implemented in a distributed manner. Likewise, components described to be distributed can be implemented in a combined manner.

The scope of the inventive concept is defined by the following claims and their equivalents rather than by the detailed description of the example embodiments. It shall be understood that all modifications and embodiments conceived from the meaning and scope of the claims and their equivalents are included in the scope of the inventive concept.

I claim:

1. An apparatus for treating food waste, comprising:
an apparatus housing with a food waste input port formed on a top surface thereof;
an open/close door that opens and closes the food waste input port;
an open/close door operating device that operates the open/close door to be opened so as to open the food waste input port, or closed so as to close the food waste input port; and
an automatic input device that enables at least part of an entrance of a food waste collection container to face with the food waste input port, in correspondence with the state of the open/close door,
wherein the open/close door operating device comprises:
an inner operation lever that extends from a rear surface of the open/close door to a downward direction;
a rotating shaft that is provided at an end of the inner operation lever;
a first outer operation lever, which extends from the rotating shaft, and of which an end moves;
a second outer operation lever, which extends from the rotating shaft, and of which an end moves;
a first power part that is connected to the end of the first outer operation lever to move the end of the first outer operation lever;
a second power part that is connected to the end of the second outer operation lever to move the end of the second outer operation lever; and
a guide part provided with a first rail and a second rail for guiding the movement of the end of the first outer operation lever and the end of the second outer operation lever;
wherein the rotating shaft is rotated by the first and second outer operating levers;
wherein the automatic input device comprises a mounting plate, on which the food waste collection container is mounted, and which moves from an initial position toward the food waste input port,
a guide part, which guides the movement of the mounting plate, and
an angle adjustment part, which adjusts an angle of the mounting plate.

2. The apparatus for treating food waste of claim 1,
wherein once the opening operation of the open/close door is completed, the mounting plate moves from the initial position toward the food waste input port.

3. The apparatus for treating food waste of claim 1,
wherein once the mounting plate moves from the food waste input port toward the initial position, the open/door operating device operates the open/close door to be closed.

4. The apparatus for treating food waste of claim 1,
wherein the angle adjustment part adjusts an angle of the mounting plate to enable the food waste collection container mounted on the mounting plate to be directed toward the food waste input port.

5. The apparatus for treating food waste of claim 1,
wherein the angle adjustment part rotates the mounting plate multiple times within a preset angle range, such that food waste in the food waste collection container mounted on the mounting plate does not remain in the food waste collection container.

6. The apparatus for treating food waste of claim 1, further comprising
a rotating shaft assembly provided within the apparatus housing to move food waste within the apparatus housing,
wherein the rotating shaft assembly comprises a rotating shaft, a plurality of agitating paddle support bars that are spaced from one another and extend from the rotating shaft in a vertical direction to the rotating shaft, an agitating paddle that is provided at an end of each of the support bars, a motor that provides power for rotating the rotating shaft, and a power transmission structure that transmits the power of the motor to the rotating shaft.

7. The apparatus for treating food waste of claim 6,
wherein the rotating shaft is reversely rotated at a preset angle, in case load higher than a nominal value occurs in the motor.

8. The apparatus for treating food waste of claim 6,
wherein the rotation of the rotating shaft is stopped, in case load higher than a nominal value occurs in the motor.

9. The apparatus for treating food waste of claim 6,
wherein the agitating paddle is provided at the agitating paddle support bar by an engagement member manufactured by a casting mold.

10. The apparatus for treating food waste of claim 6,
wherein the rotating shaft comprises a plurality of bearings provided along a circumference of an outer circumference surface of one end thereof and a plurality of bearings provided along a circumference of an outer circumference surface of the other end thereof.

11. The apparatus for treating food waste of claim 6,
wherein the power transmission structure comprises:
a interlocking sprocket provided along an outer circumference of one end of the rotating shaft;
a driving sprocket provided at the rotating shaft of the motor; and
a closed-figure shaped chain that is provided via part of the outer circumference of the coupled sprocket and part of the outer circumference of the driving sprocket, so as to enable the coupled sprocket and the driving sprocket to be incorporated with each other, wherein the plurality of the bearings are arranged at one end of the rotating shaft and positioned to each side of the coupled sprockets.

12. The apparatus for treating food waste of claim 1, further comprising a load cell provided at a lower end of the apparatus housing, so as to measure weight of food waste put into the apparatus housing.

13. The apparatus for treating food waste of claim 1, further comprising a touch screen that is provided on an outer surface of the apparatus surface to display a plurality of operation menus, and enables selection of the operation menus.

14. The apparatus for treating food waste of claim 13, further comprising a load cell provided at a lower end of the apparatus housing, so as to measure weight of food waste put into the apparatus housing, wherein the touch screen displays the weight of the waste measured by the load cell.

15. The apparatus for treating food waste of claim 13, wherein the touch screen displays menus for setting weight values to set a maximum amount of each input and a compensational value for the input of food waste compared to weight of food waste measured by the load cell.

16. The apparatus for treating food waste of claim 13, wherein the touch screen displays a screen to enable the state information of the present food waste treating apparatus to be transmitted to or stored in an external server through internet network service.

* * * * *